(12) United States Patent
Ong et al.

(10) Patent No.: US 11,786,666 B2
(45) Date of Patent: Oct. 17, 2023

(54) SHUTTLE NIB FOR CONTROL OF STOPPER DURING INJECTION

(71) Applicant: Portal Instruments, Inc., Cambridge, MA (US)

(72) Inventors: Jessica Ong, San Jose, CA (US); Robert J. Dyer, Cambridge, MA (US); Andrew Coats, Cambridge, MA (US); Nikolay Lapin, Cambridge, MA (US)

(73) Assignee: Portal Instruments, Inc., Cambridge, MA (US)

( * ) Notice: Subject to any disclaimer, the term of this patent is extended or adjusted under 35 U.S.C. 154(b) by 530 days.

(21) Appl. No.: 16/997,318

(22) Filed: Aug. 19, 2020

(65) Prior Publication Data

US 2022/0054760 A1 Feb. 24, 2022

(51) Int. Cl.
*A61M 5/315* (2006.01)
*A61M 5/31* (2006.01)

(52) U.S. Cl.
CPC .... *A61M 5/31505* (2013.01); *A61M 5/31513* (2013.01); *A61M 5/31563* (2013.01); *A61M 2005/3132* (2013.01)

(58) Field of Classification Search
CPC .......... A61M 5/31505; A61M 5/31513; A61M 5/31563; A61M 2005/3132; A61M 2005/3151; A61M 5/31515; A61M 2005/31523; A61M 5/31511; A61M 5/315; A61M 2005/3143; A61M 5/20; A61M 5/30; A61M 5/2033; A61M 2005/2086; A61M 5/31508
See application file for complete search history.

(56) References Cited

U.S. PATENT DOCUMENTS

| 2,833,280 | A | * | 5/1958 | Hein, Jr. | ............ | A61M 5/2448 222/82 |
|---|---|---|---|---|---|---|
| 5,928,202 | A | | 7/1999 | Linnebjerg | | |
| 6,142,978 | A | | 11/2000 | Niedospial, Jr. et al. | | |
| 2003/0120219 | A1 | | 6/2003 | Nielsen et al. | | |
| 2009/0097995 | A1 | | 4/2009 | Ham et al. | | |
| 2009/0137949 | A1 | * | 5/2009 | Landau | .................... | A61M 5/30 604/70 |
| 2012/0136298 | A1 | | 5/2012 | Bendix et al. | | |
| 2012/0253292 | A1 | * | 10/2012 | Ivosevic | ........... | A61M 5/31513 604/222 |
| 2020/0093994 | A1 | | 3/2020 | Clarke et al. | | |

FOREIGN PATENT DOCUMENTS

FR 2905274 A1 * 3/2008 .............. A61M 5/20

OTHER PUBLICATIONS

English Translation of FR 2905274 A1 (Abstract, Description, Drawings) (Year: 2023).*
International Search Report, dated Jan. 19, 2022 (4 Pages).

* cited by examiner

*Primary Examiner* — Katherine H Schwiker
*Assistant Examiner* — Phoebe Anne Staton
(74) *Attorney, Agent, or Firm* — Occhiuti & Rohlicek LLP

(57) ABSTRACT

A needleless injection system includes a pusher that pushes a plunger within a tapered bore of a cartridge. The pusher includes a nib, the tip of which is a ball.

17 Claims, 7 Drawing Sheets

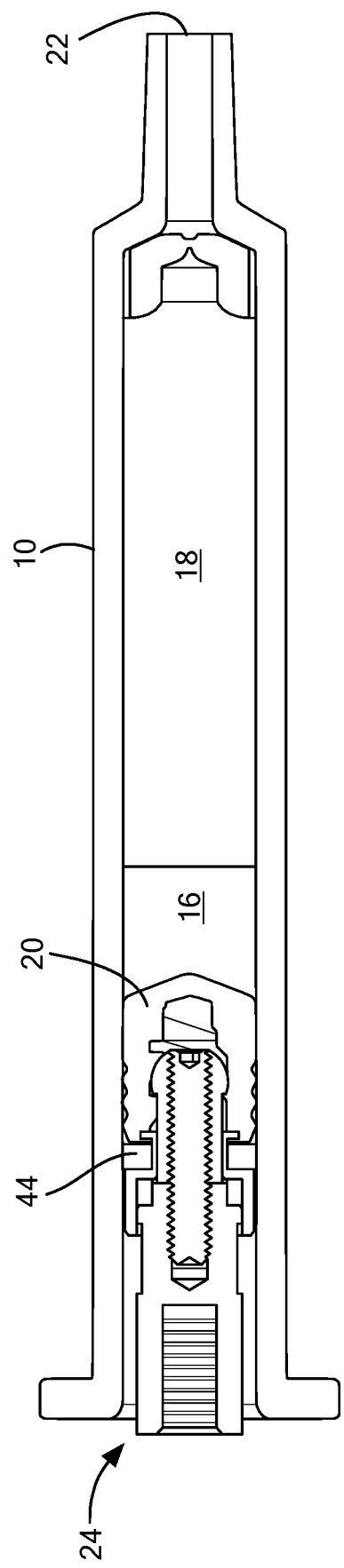
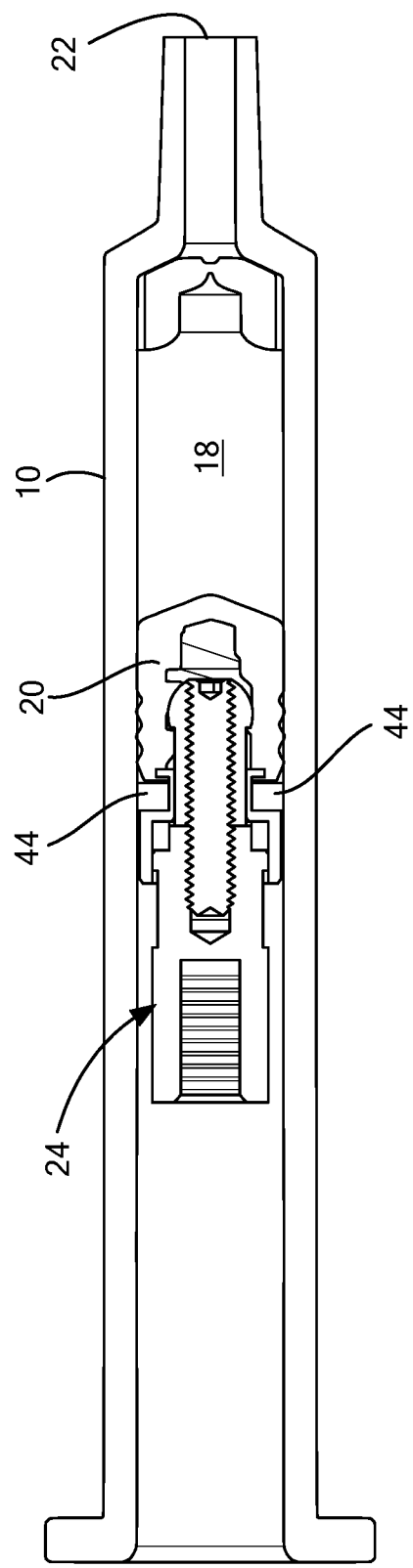
FIG. 11
FIG. 12

SHUTTLE NIB FOR CONTROL OF STOPPER DURING INJECTION

FIELD OF INVENTION

This invention relates to delivery of injectates (e.g., drugs, medicine), and in particular, to trans-dermal delivery.

BACKGROUND

Known methods of delivering an injectate through the skin include the use of a hollow needle through which an injectate is injected. This method poses certain disadvantages. For example, needles can inflict pain. And even in those cases where pain is minimal, needles create an anticipation of pain that many find disconcerting.

An alternative method is to drive the injectate through the skin using some type of force. An example of such a force is that provided by a burst of high pressure. Such a pressure can simultaneously open gaps between skin cells and drive the injectate through those gaps.

An apparatus for carrying out such an injection typically includes a barrel having an orifice at a distal end thereof. Within the barrel is a plunger that can be moved distally. Between the plunger and the orifice is a dose of the injectate. To carry out the injection, the plunger is moved distally to force the injectate through the orifice under high pressure. During this injection process, the plunger may sustain high forces that cause deformation. This deformation adversely affects performance.

SUMMARY

In one aspect, the invention features a needleless injection system that includes a pusher that pushes a plunger within a tapered bore of a cartridge. The pusher includes a nib having a ball at a distal end thereof.

In some embodiments, the ball has a diameter selected such that, when inserted into a cavity in the plunger, the ball exerts a radial pressure to push the plunger against an inner wall of the bore.

In other embodiments, the ball is a rounded protuberance disposed at a distal end of the nib.

In yet other embodiments, the pusher further comprises an ejector that causes the nib to disengage from the plunger. Among these are embodiments in which the ejector includes a spring coupled to a shuttle so as to cause the shuttle to move distally towards the ball in response to expansion of the spring.

In other embodiments, the pusher comprises a backup ring disposed proximal to the ball, the backup ring being configured to deflect a force exerted by the plunger along a radial direction. Among these embodiments are those in which the backup ring has a slit. Also, among these are embodiments in which the backup ring has a gap defined by first and second faces that face each other, each of the first and second faces having a normal vector that has components in both the distal direction and a direction normal to the distal direction.

Other embodiments include those in which the pusher comprises a shuttle that is configured to move axially relative to the nib. Since the bore is tapered, it has a minimum and a maximum diameter. In some of these embodiments, the shuttle's diameter is less than the tapered bore's minimum diameter.

Also among the embodiments are those in which the pusher comprises a base and screw that holds the nib to the base. Among these are embodiments in which the screw is a set screw and those in which it is a grub screw.

Yet other embodiments feature a ring that causes at least a portion of a proximally directed axial force to be deflected into the radial direction.

Other embodiments features a plunger that has a cavity formed therein. The cavity opens at a distal end thereof to receive and envelope the ball during the injection process.

Still other embodiments include those in which the plunger includes a circumferential rib around a surface thereof. In these embodiments a cavity within the plunger and the ball are configured such that the ball, when inserted into the cavity of the plunger, applies a pressure on the inner wall where the rib contacts the inner wall.

Other embodiments include those in which the pusher comprises a ring that expands in response to a reaction force that results from acceleration of the plunger.

In another aspect, the invention features a method that includes forcing injectate through an orifice of a cartridge having a tapered bore that holds the injectate at a distal end thereof. Forcing the injectate through the orifice includes causing a ball at a distal tip of a nib of a pusher to be enveloped by a cavity within a plunger that is disposed within the bore and using the pusher to accelerate the plunger through the tapered bore of the cartridge towards the orifice.

Some practices of the invention include, after having forced the injectate through the orifice, exerting a distal force on the plunger, thereby removing the ball from the cavity.

Other practices are those in which accelerating the plunger includes deflecting at least a portion of an axially-directed force in a radial direction, the axially-directing force being one that arises from accelerating the plunger through the tapered bore.

Still other practices are those in which accelerating the plunger includes expanding a diameter of a ring that fills a gap between a wall of the tapered bore and the pusher.

Yet other practices include causing the ball to apply an axially varying radial force through the plunger and onto a wall of the tapered bore.

In some practices, forcing the injectate through the orifice further includes applying a static radial force onto a wall of the tapered bore and simultaneously applying a dynamic radial force onto the wall.

As used herein, and as should be apparent from the figures, the term "ball" is not restricted to a sphere but instead refers to a rounded protuberance that achieves the advantages described herein.

These and other features will be apparent from the following detailed description and the accompanying figures, in which:

BRIEF DESCRIPTION OF THE DRAWINGS

FIG. 11 shows the nib after having engaged the plunger;

FIG. 12 shows the plunger just after having made contact with the injectate in the medicinal chamber;

DETAILED DESCRIPTION

Figure 1:
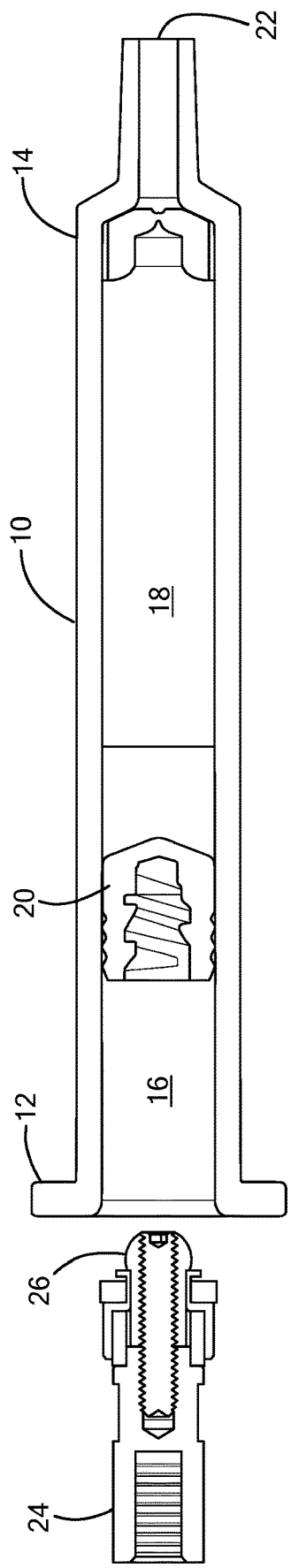
FIG. 1 shows a plunger that defines a medicinal chamber in a cartridge and a nib that engages the plunger during injection.

FIG. 1 shows a cartridge 10 that extends along a longitudinal axis between a proximal end 12 and a distal end 14. A tapered bore 16 extends along this axis. As a result of its taper, the bore 16 has a diameter that decreases continuously in the distal direction. Within the bore 16 is an axially movable plunger 20 that divides the bore 16 into a distal portion and a proximal portion.

During injection, a rapid movement of a plunger 20 in the distal direction reduces the volume of an injectate chamber 18, thus forcing the injectate through an orifice 22 at the distal end 14. This rapid movement arises from a pusher 24 that causes a nib 26 at a distal end thereof to move distally until it engages the plunger 20. Upon engaging the plunger 20, the nib 26 continues to move distally. As it does so, it pushes the plunger 20 so as to force injectate through the orifice 22.

Once the plunger 20 has been pushed as far as it will go, the injection is complete. At this point, the nib 26 disengages from the plunger 20 and retracts along the longitudinal axis. The cartridge 10, having been emptied, can be discarded.

Figure 2:
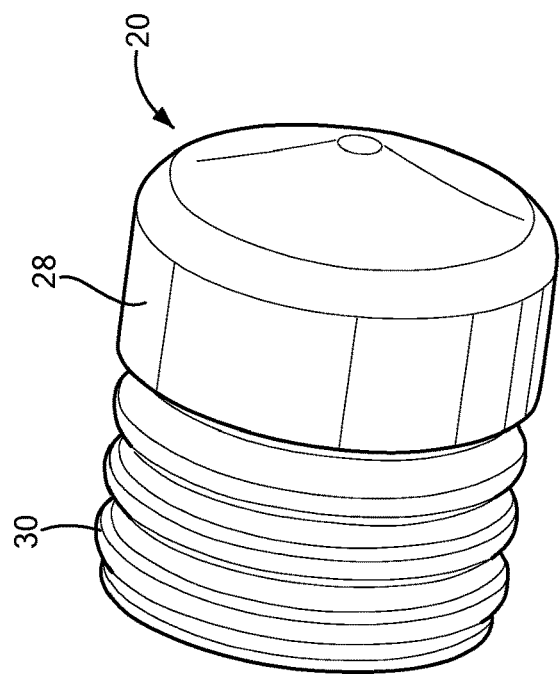
FIG. 2 shows details of the plunger in FIG. 1.

As shown in FIG. 2, a typical plunger 20 is an approximately cylindrical structure that is made of a compliant material. The use of a compliant material enables the plunger 20 to form a sliding seal at the cartridge's inner wall. During injection, this seal sustains pressures that can briefly approach or exceed twenty-five newtons per square millimeter.

Figure 3:
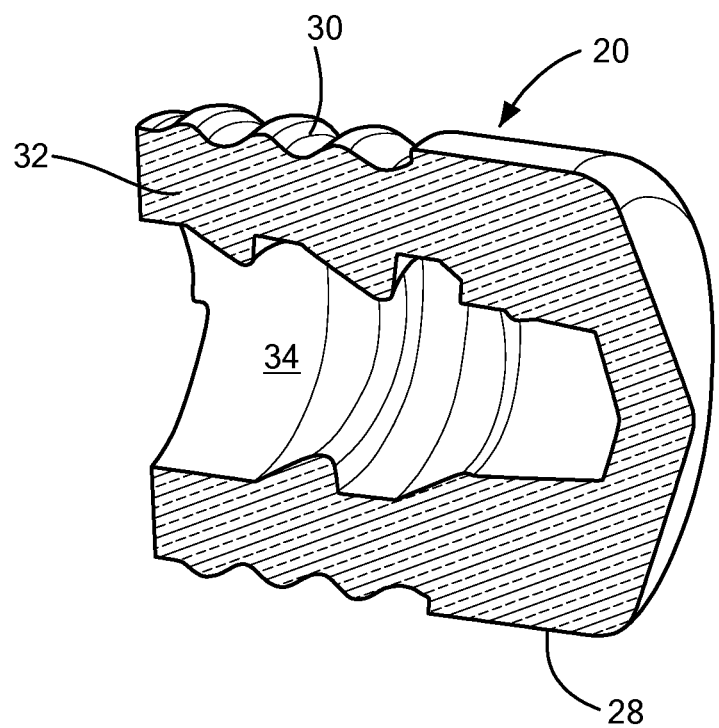
FIG. 3 is a cross section of the plunger shown in FIG. 2, showing the plunger cavity that receives the distal end of a nib.

A proximal portion of the plunger 20 has a ribbed surface 30 and the distal portion of the plunger 20 has a smooth surface 28. As shown in the cut-away view of FIG. 3, the wall that forms the ribbed surface 30 also forms a neck 32 that opens up into a wider cavity 34. During injection, the distal portion of the nib 26 passes through the neck 32 and into the cavity 34. It then accelerates the plunger 20 distally so as to force the injectate out of the cartridge.

During its brief interaction with the nib 26, the plunger 20 experiences high forces. These forces can damage the plunger 20 or otherwise interfere with its effectiveness.

One source of difficulty arises from the compliance of the material from which the plunger 20 is made. Although this compliance is useful for forming a good seal between the plunger 20 and the cartridge wall, it is not so useful for sustaining high forces. As a result, the plunger 20 may collapse during injection.

Another source of difficulty is that the plunger 20 may tear during injection. This can result from shearing caused by the plunger's high velocity in combination with friction that results from limited siliconization of the various sliding surfaces.

In other cases, it is possible to compromise the integrity of the seal between the plunger 20 and the cartridge's inner wall. This can result in spray back, as injectate travels proximally instead of distally.

Yet another source of difficulty arises with ingress of fluid into the spaces between the ribs 36 on the ribbed surface 30. This can compromise the sterility of the medicinal chamber.

Figure 4:
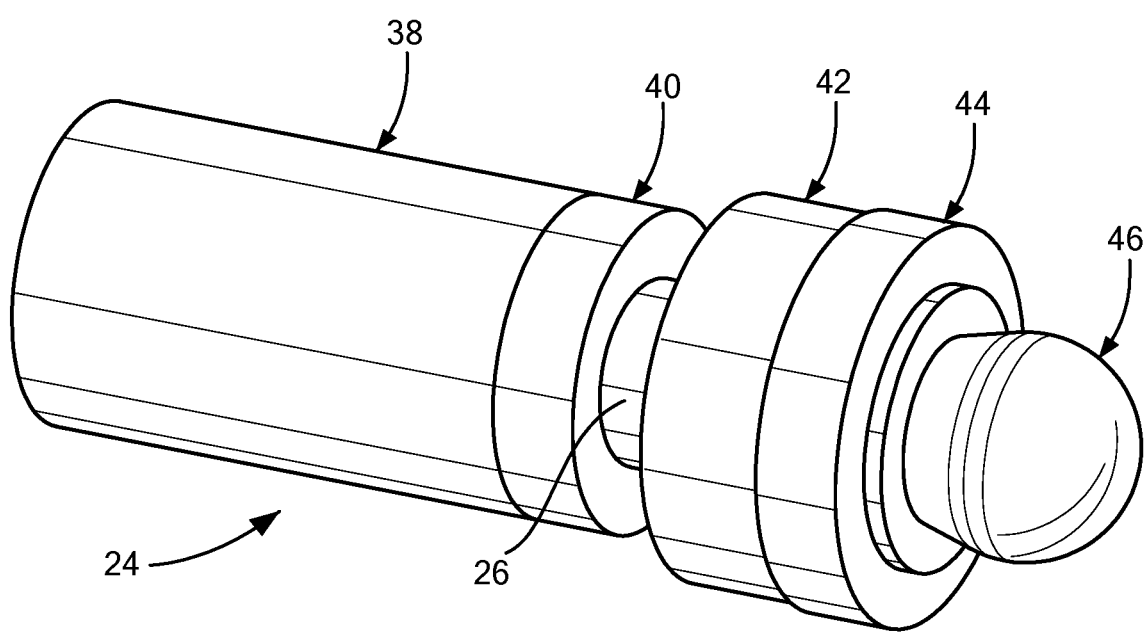
FIG. 4 is an isometric view of the nib shown in FIG. 1.

A pusher 24 having a nib 26 as shown in FIG. 4 reduces the likelihood of at least the foregoing difficulties.

Referring now to FIG. 4, the illustrated pusher 24 features a base 38 at its proximal end. At the distalmost end of the base 38 is a compressed spring 40 (e.g., formed of stainless steel) that, when released, causes a shuttle 42 (e.g., formed of 17-4 PH stainless steel) to move axially in the distal direction. The shuttle's diameter is slightly smaller than the bore's smallest diameter. This ensures that the shuttle 42 will always fit inside the bore 16.

A backup ring 44 lies distal to the shuttle 42. The backup ring 44 is slightly larger than the bore's largest diameter. This permits it to compensate for the variable gap between the shuttle 42 and the wall. Unlike the rigid shuttle 42, the backup ring 44 is compressible (e.g., formed of Polytetralluomethylene (PTFE) plastic. Therefore, the backup ring 44 is able to reduce its diameter to follow the bore's taper.

At its very tip, just distal to the backup ring 44, the nib 26 has a ball 46 (e.g., formed of Polytetrafluoroethylene (PTFE) plastic) at a distal tip thereof. A set screw 48, best seen in the cross section in FIG. 5, couples the nib 26 to the base 38.

The ball 46 at the distal end of the nib 26 is sufficiently large to fill most of the cavity 34. This permits the ball 46 to exert a radially outward pressure that supports the plunger 20 during the injection. This radially outward pressure forces the plunger 20 against the cartridge wall. The radial force thus exerted suppresses the injectate's tendency to escape by flowing in the proximal direction between the plunger 20 and the cartridge's inner wall. By filling most of the cavity 34, the ball 46 tends to stiffen the plunger 20. This promotes energy transfer since energy that would otherwise be spent deforming the plunger 20 can instead be used to accelerate the plunger 20.

As the cavity 34 merges into the neck 32 at the proximal end of the plunger 20, its diameter decreases to the point at which it is slightly smaller than that of the ball 46. This permits the plunger 20 to relax, thus decreasing friction and inhibiting the possibility of damaging the plunger 20. This also means that once the ball 46 has forced its way into the cavity 34, some effort is required to remove it. An ejection mechanism, to be described below in connection with the spring 40 and the shuttle 42, assists in doing so.

A particular advantage of the ball 46 is that it exerts a radial pressure that varies along the axis of the plunger 20. A slight radial pressure offers the benefit of promoting a better seal. On the other hand, radial pressure also increases frictional force. However, the extent to which radial pressure increases frictional force also depends on the extent of the area over which the radial pressure is applied. This frictional force will resist the plunger's movement.

In general, application of a radial pressure over a small area will be sufficient to promote a better seal. The marginal benefit of applying that same radial pressure over a larger area is minimal. In contrast, the marginal detriment associated with applying that pressure over a larger area, in terms of the increased friction, is significant.

Figure 6:
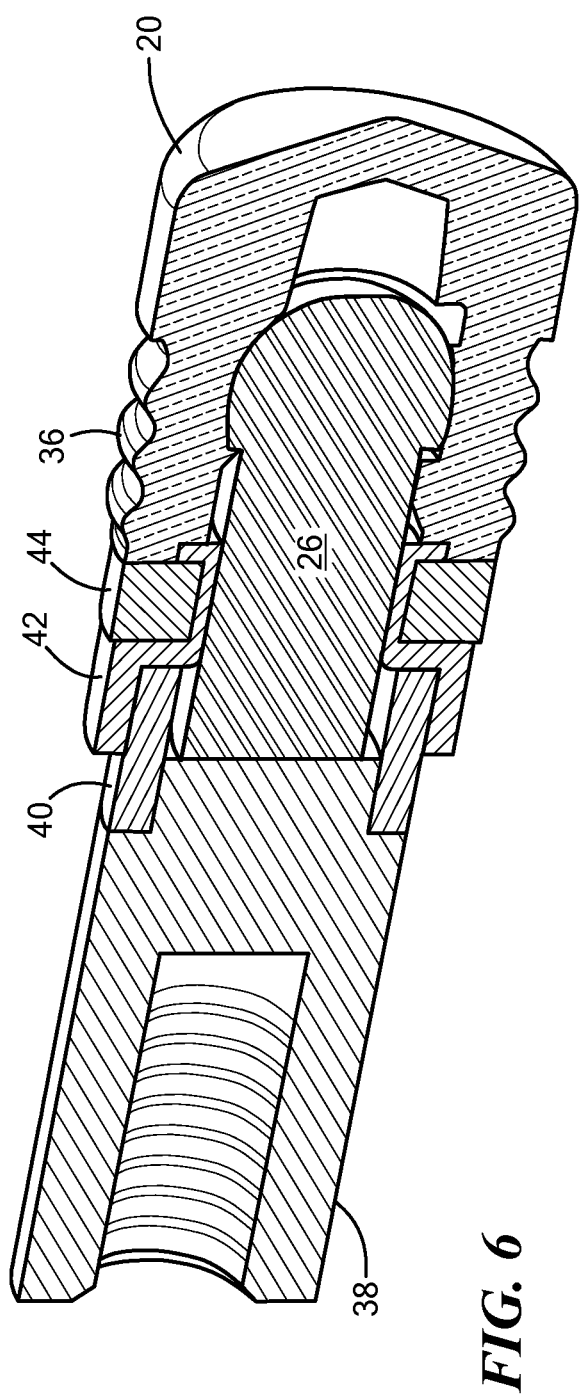
FIG. 6 is a cut-away view that shows the nib inserted into the plunger.

By providing a radial pressure only over a small area, the ball 46 is able to promote a good seal but without excessively increasing friction. Additionally, the ball 46 permits the application of radial pressure at an optimal location, where it counts most, while simultaneously avoiding unnecessary radial pressure over an extended area. In the illustrated embodiment, the ball 46 applies most of the pressure at the distalmost rib 36, as shown in FIG. 6.

As can be seen in FIG. 4, the backup ring 44 lies between the ball 46 and the shuttle 42. The backup ring's diameter is slightly larger than that of the bore 16. This ensures that the backup ring 44 is always compressed against the cartridge's inner wall, where it forms a sliding seal that resists the plunger's tendency to deform and extrude axially along the inner wall during the injection. Because the backup ring 44 both presses against the inner wall and slides, it is particularly useful for it to be made of a slippery material with a low friction coefficient. A particularly suitable material is polytetrafluoroethylene.

Figure 7:
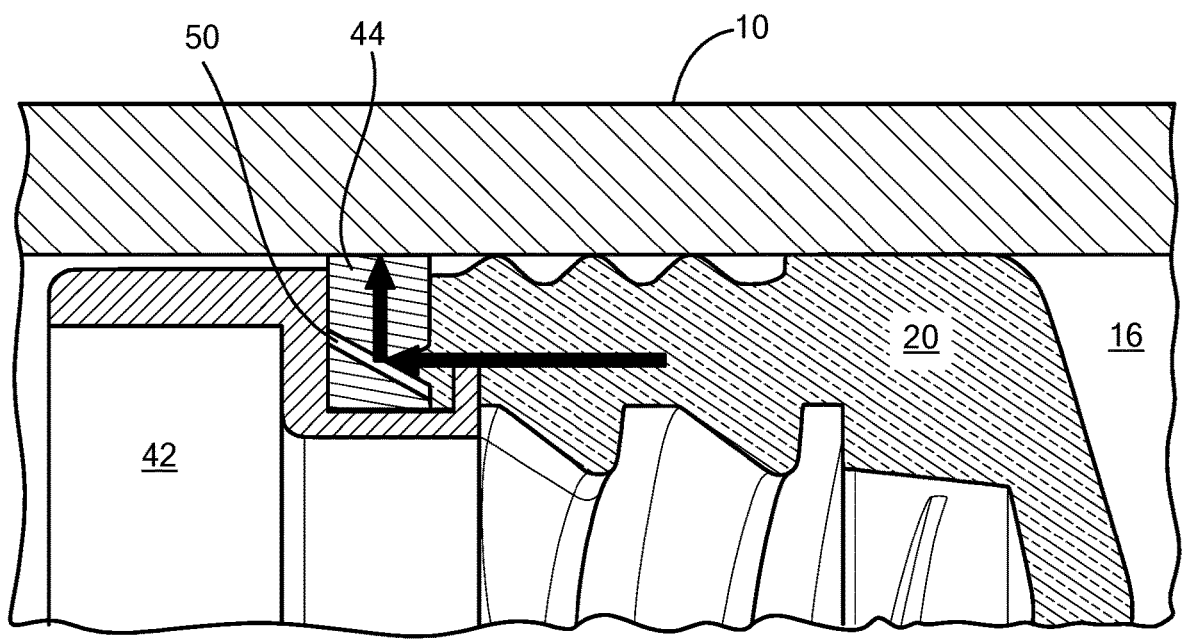
FIG. 7 shows response of the backup ring to an axial force.

Referring to FIG. 7, during injection, the backup ring 44 exerts a force against the plunger 20. Indeed, it is this force that causes the plunger's distal acceleration. Naturally, the plunger 20 exerts an equal and opposite reaction force against the ring 44.

A useful feature of the backup ring 44 is the manner in which it harnesses this reaction force to promote a better seal. Rather than simply resisting this reaction force, the backup ring deflects it against the inner wall. This promotes its ability to seal and also to resist the plunger's tendency to extrude along the axial direction.

Figure 8:
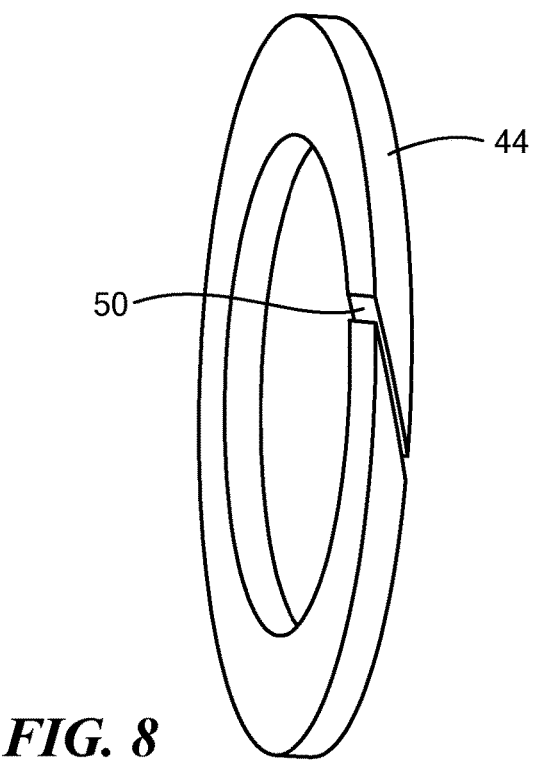
FIG. 8 shows an isometric view of the backup ring in FIG. 7.

To deflect the reaction force, the backup ring 44 is backup by a slit 50, as shown in FIG. 7 and in isometric view in FIG. 8. As seen best in FIG. 8, the slit is not transverse to the faces of the backup ring; rather, the slit is angular to the faces of the backup ring. This slit 50 uses the reaction force to radially expand the ring 44. This radial expansion exerts a radial force against the wall, which in turn promotes sealing. As a result of a slit 50, the backup ring 44 has two surfaces that face each other. Each surface has a normal vector. The normal vectors have non-zero components in both the axial direction and in a direction perpendicular to the axial direction. These surfaces decompose the reaction force's vector into two components, one of which is directed against the wall of the cartridge 10.

At the end of the injection, the ball 46 will still be inside the cavity 34. Thus, if the nib 26 is simply pulled out of the cartridge 10, the plunger 20 is apt to come with it. To prevent this, the pusher 24 features an ejector that uses the spring 40 to eject the plunger 20 from the nib 26 after the injection.

Figure 5:
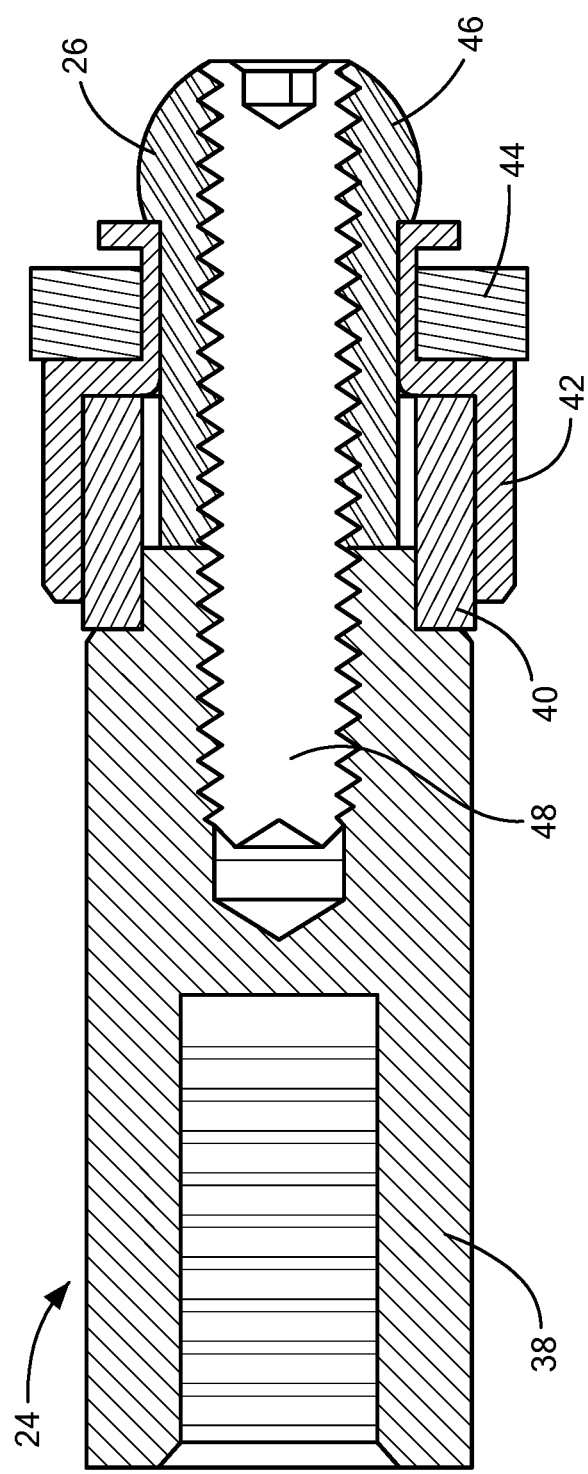
FIG. 5 shows a cross-section of the nib shown in FIG. 4 in its retracted state.
Figure 9:
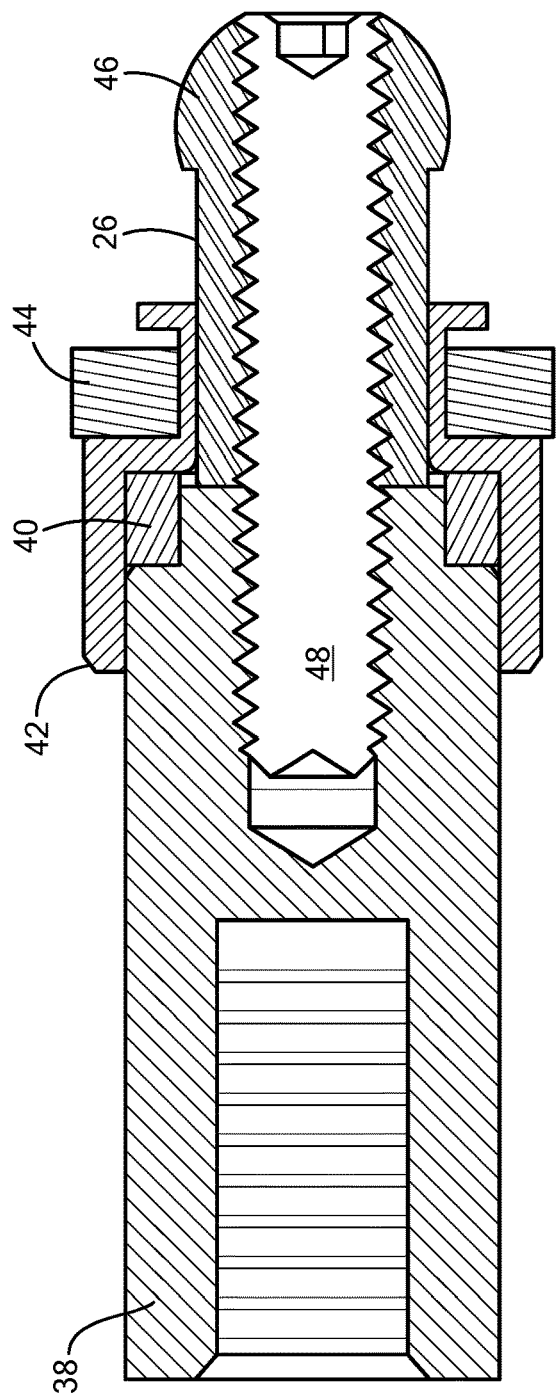
FIG. 9 shows a cross-section of the nib shown in FIG. 4 in its extended state.

In response to the state of the spring 40, the nib 26 transitions between a retracted state, as shown in FIG. 5, and an extended state, as shown in FIG. 9. In the extended state, the spring 40 is compressed and the ball 46 is furthest from the shuttle 42. This is the state used during injection. In the retracted state, shown in FIG. 5, the spring 40 is compressed and the ball is closest to the shuttle 42. This is the state used to disengage the plunger 20 from the nib 26.

At the end of the injection, when it is time to disengage the plunger 20 from the nib 26, the spring 40 is released and allowed to expand. In doing so, it pushes against the shuttle 42. This causes the shuttle 42 to push against the plunger 20. This pushes the plunger 20 forward so that it releases the ball 46, thus separating the plunger 20 from the nib 26. With the spring 40 now uncompressed, the nib 26 is now in the extended state as shown in FIG. 5.

The injection sequence begins with the pusher 24 outside the cartridge 10 as shown in FIG. 1. FIGS. 10-14 show milestones in the remainder of the injection process and its aftermath.

Figure 10:
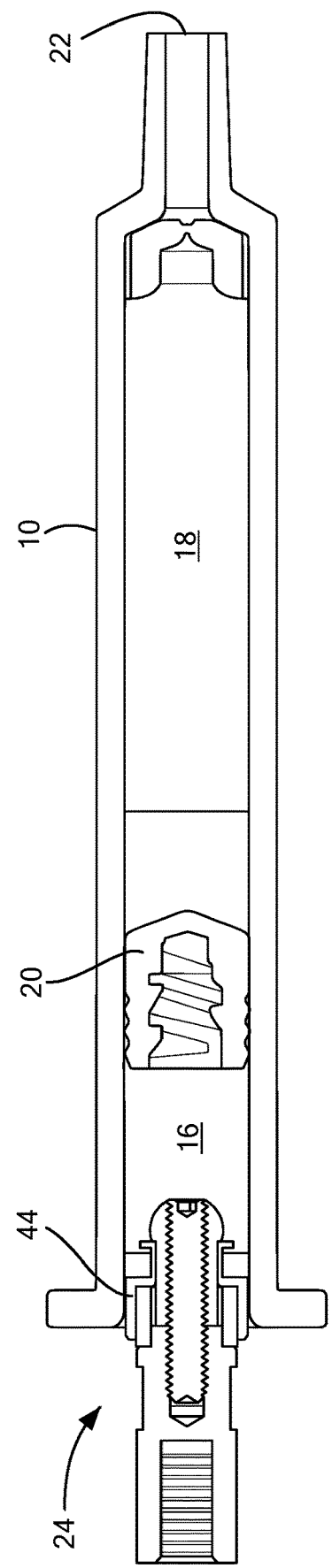
FIG. 10 shows the nib after having entered the bore.

In FIG. 10, the pusher 24 has just entered the cartridge 10. The backup ring 44, having a diameter slightly larger than that of the bore 16, has now become compressed. It will continue to be compressed even further as it travels distally down the bore 16.

FIG. 11 shows the nib 26 and the plunger 20 just after having engaged. During injection, the force is more than sufficient to compress the spring 40. With the spring 40 compressed, the shuttle 42 is free to travel in the proximal direction. The nib 26 thus assumes the extended state shown in FIG. 9.

FIG. 12 shows the plunger 20 after the pusher 24 has pushed it far enough so that it has begun applying pressure to the injectate. It is here that the risk of leakage begins. However, as a result of the ball 46, the plunger 20 is forced against the wall, thus suppressing the injectate's tendency to escape the pressure by flowing proximally past the plunger 20 instead of out the orifice 22.

Once the plunger 20 reaches the injectate, there is now a more significant force to resist the plunger's further distal movement. As a result, the plunger 20 needs all the energy it can get to continue its distal movement. The ball's presence within the cavity reinforces the plunger 20 and thus prevents applied energy from being wasted in compressing the plunger 20 instead of assisting in its forward motion.

Figure 13:
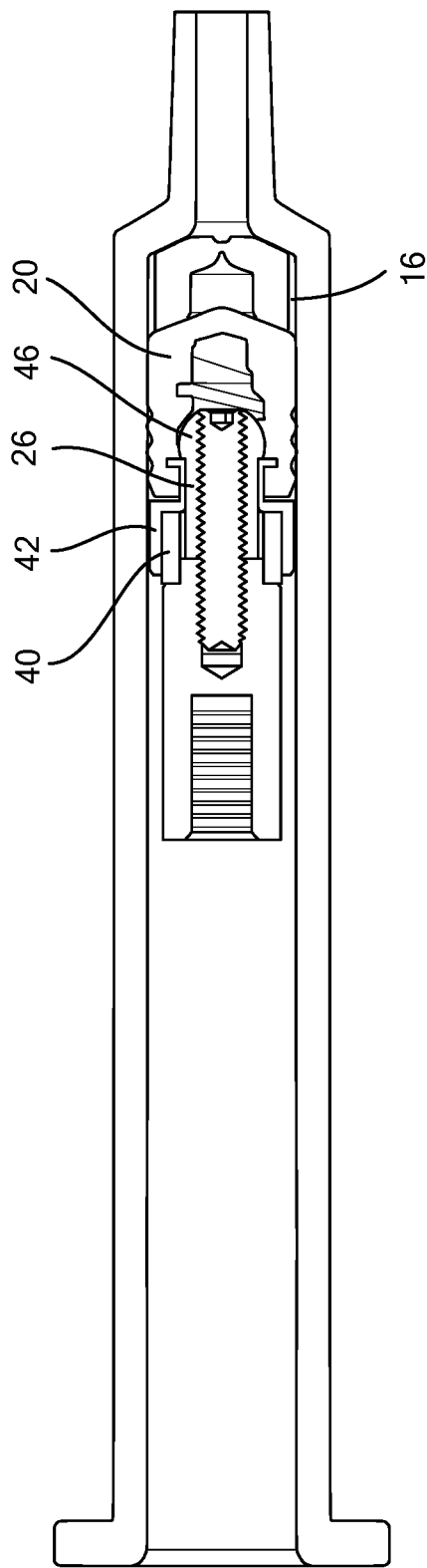
FIG. 13 shows the plunger at the end of the injection.

At FIG. 13, all the injection is complete. The nib 26 retracts and the spring 40 expands, thus causing the shuttle 42 to move distally to disengage the ball 46 from the cavity. With the ball 46 having been thus disengaged, the nib 26 can be retracted while leaving the plunger 20 at the distal end of the bore 16. With its proximal motion unhindered by the additional friction from the tightly wedged plunger 20, this makes it much easier to retract the nib 26.

Figure 14:
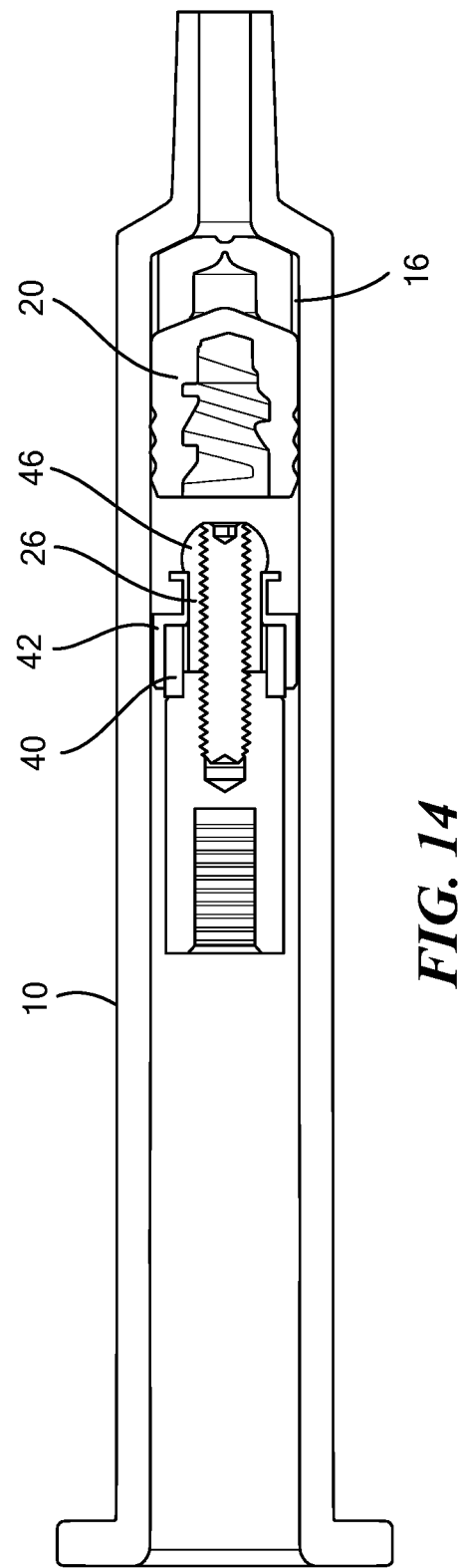
FIG. 14 shows the nib after having been separated from the plunger.

FIG. 14 shows the nib 26, now free of the plunger 20 and safely on its way out of the cartridge 10. The plunger 20 remains at the bottom of the cartridge 10.

Having described the invention, and a preferred embodiment thereof, what is claimed as new and secured by Letters Patent is:

1. An apparatus comprising a pusher for injecting an injectate through a patient's skin, wherein said pusher is configured to push a plunger in a distal direction through a tapered bore of a cartridge that contains said injectate within a medicinal chamber at a distal end thereof, thereby forcing said injectate out of an orifice at a distal end of said cartridge, wherein said pusher comprises a nib having a ball at a distal end thereof, and wherein said pusher further comprises a shuttle that is configured to move axially relative to said nib, said shuttle having a diameter that is less than a minimum diameter of said tapered bore.

2. The apparatus of claim 1, wherein said ball has a diameter selected such that, when inserted into a cavity in said plunger, said ball exerts a radial pressure to push said plunger against an inner wall of said bore.

3. The apparatus of claim 1, wherein said ball is a rounded protuberance at the distal end of said nib.

4. The apparatus of claim 1, wherein said pusher is configured to cause said nib to disengage from said plunger.

5. The apparatus of claim 1, wherein said pusher comprises a spring, wherein said spring is coupled to said shuttle so as to cause said shuttle to move distally towards said ball in response to expansion of said spring.

6. The apparatus of claim 1, wherein said pusher comprises a backup ring disposed proximal to said ball, said backup ring being configured to deflect a force exerted by said plunger along a radial direction.

7. The apparatus of claim 1, wherein said pusher comprises a backup ring disposed proximal to said ball, said backup ring having a slit.

8. The apparatus of claim 1, wherein said pusher comprises a backup ring disposed proximal to said ball, said backup ring having a gap defined by first and second faces that face each other, each of said first and second faces having a normal vector that has components in both the distal direction and a direction normal to the distal direction.

9. The apparatus of claim 1, wherein the pusher comprises a backup ring that has a diameter that is larger than the largest diameter of the bore.

10. The apparatus of claim 1, wherein said plunger comprises a wall forming a cavity that opens at a proximal end thereof and wherein said cavity envelopes said ball.

11. The apparatus of claim 1, wherein said plunger comprises a circumferential rib around a surface thereof, wherein said bore has an inner wall, wherein said ball, when inserted into a cavity of said plunger, applies a pressure on said inner wall where said rib contacts said inner wall.

12. An apparatus comprising a pusher for injecting an injectate through a patient's skin, wherein said pusher is configured to push a plunger in a distal direction through a tapered bore of a cartridge that contains said injectate within a medicinal chamber at a distal end thereof, thereby forcing said injectate out of an orifice at a distal end of said cartridge, wherein said pusher comprises a nib having a ball at a distal end thereof, wherein said pusher comprises a ring that expands in response to a reaction force that results from acceleration of said plunger.

13. A method comprising forcing an injectate through an orifice of a cartridge having a tapered bore that holds said injectate at a distal end thereof, wherein forcing said injectate through said orifice comprises causing a ball at a distal tip of a nib of a pusher to be enveloped by a cavity within a plunger that is disposed within said bore and using said pusher to accelerate said plunger through said tapered bore of said cartridge towards said orifice and wherein accelerating said plunger comprises expanding a diameter of a ring that fills a gap between a wall of said tapered bore and said pusher.

14. The method of claim 13, further comprising, after having forced said injectate through said orifice, exerting a distal force on said plunger, thereby removing said ball from said cavity.

15. The method of claim 13, further comprising applying dynamic radial force, wherein accelerating said plunger comprises deflecting at least a portion of an axially-directed force in a radial direction, said axially-directing force being one that arises from accelerating said plunger through said tapered bore.

16. The method of claim 13, further comprising causing said ball to apply an axially varying radial force through said plunger and onto a wall of said tapered bore.

17. The method of claim 13, wherein forcing said injectate through said orifice further comprises applying a static radial force onto a wall of said tapered bore and simultaneously applying a dynamic radial force onto said wall.

* * * * *